(12) United States Patent
Fredriksson et al.

(10) Patent No.: US 11,969,608 B2
(45) Date of Patent: Apr. 30, 2024

(54) SYSTEM AND METHOD FOR PASSIVE ION RADIOTHERAPY TREATMENT PLANNING AND DELIVERY

(71) Applicant: RaySearch Laboratories AB, Stockholm (SE)

(72) Inventors: Albin Fredriksson, Stockholm (SE); Erik Engwall, Hägersten (SE); Kjell Eriksson, Bålsta (SE); Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 321 days.

(21) Appl. No.: 17/415,019

(22) PCT Filed: Dec. 12, 2019

(86) PCT No.: PCT/EP2019/084801
§ 371 (c)(1),
(2) Date: Jun. 17, 2021

(87) PCT Pub. No.: WO2020/126786
PCT Pub. Date: Jun. 25, 2020

(65) Prior Publication Data
US 2022/0040500 A1  Feb. 10, 2022

(30) Foreign Application Priority Data
Dec. 20, 2018 (EP) ..................... 18214823

(51) Int. Cl.
*A61N 5/10* (2006.01)
(52) U.S. Cl.
CPC ......... *A61N 5/1031* (2013.01); *A61N 5/1078* (2013.01); *A61N 2005/1087* (2013.01)

(58) Field of Classification Search
CPC ................ A61N 5/1031; A61N 5/1078; A61N 2005/1087; A61N 5/103
See application file for complete search history.

(56) References Cited

U.S. PATENT DOCUMENTS

| 10,143,856 B2 | 12/2018 | Siljamäki et al. |
| 2004/0165696 A1* | 8/2004 | Lee ........................ G16H 20/40 378/65 |

(Continued)

FOREIGN PATENT DOCUMENTS

| CN | 105359223 A | 2/2016 |
| CN | 107708807 A | 2/2018 |

(Continued)

OTHER PUBLICATIONS

Seco et al., "Proton Arc Reduces Range Uncertainty Effects and Improves Conformality Compared With Photon Volumetric Modulated Arc Therapy in Stereotactic Body Radiation Therapy for Non-Small Cell Lung Cancer," International Journal Radiation Oncology Biology Physics, vol. 87, No. 1, pp. 188-194, 2013.

(Continued)

*Primary Examiner* — Kiho Kim
(74) *Attorney, Agent, or Firm* — Faegre Drinker Biddle & Reath LLP

(57) ABSTRACT

A method of generating a radiotherapy plan for ion therapy, wherein the beam (6) is shaped by means of passive devices is arranged to allow variation in settings of at least one of the passive devices and/or the MU during the delivery of the beam and to control the movement of the patient and/or the beam in such a way as to create an arc. The arc is preferably a continuous arc or includes at least one continuous sub-arc. The method may include forward planning or optimization. In the latter case, the optimization uses an optimization problem set up to allow variation in settings of at least one of the range modulating device (9), the aperture element (11)

(Continued)

and the MU during the delivery of the arc. Computer programs control the planning and the delivery.

14 Claims, 2 Drawing Sheets

(56) References Cited

U.S. PATENT DOCUMENTS

| | | | | |
|---|---|---|---|---|
| 2009/0080602 | A1* | 3/2009 | Brooks | A61B 6/4258 |
| | | | | 378/65 |
| 2016/0199667 | A1* | 7/2016 | Flynn | G21K 1/04 |
| | | | | 600/1 |
| 2019/0290931 | A1* | 9/2019 | Ranganathan | A61N 5/103 |

FOREIGN PATENT DOCUMENTS

| | | | | |
|---|---|---|---|---|
| CN | 108025183 A | | 5/2018 | |
| EP | 3 108 932 A1 | | 12/2016 | |
| EP | 3108932 A1 | * | 12/2016 | ........... A61N 5/1031 |
| JP | 2011-521721 A | | 7/2011 | |
| JP | 2014-209485 A | | 11/2014 | |
| WO | WO-2016/014422 A1 | | 1/2016 | |
| WO | WO-2017/156419 A1 | | 9/2017 | |

OTHER PUBLICATIONS

Sandison et al., "Phantom Assessment of Lung Dose from Proton Arc Therapy," International Journal Radiation Oncology Biology Physics, vol. 38, No. 4, pp. 891-897, 1997.

First Office Action issued Jan. 8, 2024 in Chinese Application No. 201980076153.5.

\* cited by examiner

SYSTEM AND METHOD FOR PASSIVE ION RADIOTHERAPY TREATMENT PLANNING AND DELIVERY

This application is the National Stage of International Application No. PCT/EP2019/084801, filed Dec. 12, 2019, and claims benefit of European Patent Application No. 18214823.9, filed Dec. 20, 2018, the entire contents of which are incorporated by reference herein.

TECHNICAL FIELD

The present invention relates to a system and a method for planning of passive ion radiotherapy treatment, in which a tumour is targeted with a beam of ions, such as protons or heavier ions like carbon.

BACKGROUND

Radiotherapy is commonly used for treating diseases such as cancer. Various types of radiation sources may be used. The predominant type of radiation used today is photon radiation. Although more expensive than photon radiotherapy, ion-based therapy methods, such as proton and carbon therapy, are becoming more common because of their advantages. In particular, the deposition of dose can be controlled more precisely because an ion beam has finite range determined by its initial energy. Also, an ion will deposit most of its energy close to the depth where it stops, in the area known as the Bragg peak.

Passive ion therapy involves applying a broad field of radiation and using physical elements, referred to as passive devices, to shape the beam to match the target as precisely as possible. The maximum beam energy will control the maximum range of the ions in the patient. The lateral shape of the beam is controlled by an aperture in the beam line, such as a block or a collimator of a non-permeable material, e.g. tungsten or brass. The width of the high dose region, i.e. the Spread Out Bragg Peak (SOBP), is created by modulating the energy of individual ions and is controlled by for example a range modulator or ridge filter. Typically, a range compensator is also used, which is placed in the beam trajectory to affect the maximum depth of the beam differently in different lateral positions in the patient anatomy. The range compensator shortens the local range of the ion beam and is non-uniformly shaped to conform to the distal edge of the tumour. Traditionally, the settings for a passive ion therapy plan, i.e. the shape of the aperture, the range and width of the SOBP and the shape of the range compensator, are created by forward planning.

Arc therapy, in which a beam is rotated around the patient during therapy, is being explored increasingly in photon therapy, and more recently in proton therapy. The main advantages are lower entrance doses, shorter delivery times and, for proton therapy, also a more beneficial Linear Energy Transfer (LET) distribution. However, ion-based delivery systems, such as proton delivery systems, currently have heavy gantries and it is a challenge to rotate the gantry fast enough to deliver arc therapy of a sufficient quality in an acceptable amount of time. Well-balanced, fast rotating gantries are expensive and require more space than a fixed beam line. Arc therapy for ions have mainly been considered for actively scanned systems but can also have advantages in passive ion-based therapy.

Sandison et al., International Journal of Radiation oncology*Biology*Physics, Vol. 38, No. 4, 1997 discloses an experimental setup for passive proton arc therapy in which a rotating model of a human torso was irradiated from a system comprising a collimator, a scatterer and a range modulator. It was found that proton arc treatments could give a more uniform dose coverage of the target volume paired with a reduction in integral lung dose, compared to electron arc therapy. The method according to this paper enables a uniform target dose but provides no means of protecting the OARs.

Seco et al., International Journal of Radiation oncology*Biology*Physics, 87 (2013) discusses advantages for proton arc therapy compared to photon arc therapy (VMAT). They compare both passive and active scanning proton arcs with the conventional photon technique. A simulation study is presented, in which the arcs are discretized into 8-10 beam angles and the passive devices are created through forward planning. No information is given on how a plan for a passive arc with continuous rotation could be achieved.

SUMMARY

It is an object of the present invention to provide an improved method for ion-based arc therapy.

The invention relates to a method of generating a radiotherapy plan for ion therapy designed to expose a patient to ion radiation delivered as a beam, wherein the beam is shaped by means of passive devices including: a range modulating device for creating a spread out Bragg peak, SOBP, and an aperture element for shaping the beam laterally, said method being arranged to allow variation in settings of at least one of the range modulating device, the aperture element and the the segment MU, during the delivery of the beam and to control the movement of the patient and/or the beam in such a way as to create an arc.

The arc is a continuous arc or includes at least one continuous sub-arc. This allows for faster delivery of the radiation. In this document, the term arc means that the beam is caused to move across the patient so that it will enter the patient's body in different positions. A continuous arc or sub-arc means that the radiation is on during the movement of the beam for the whole arc or for the sub-arc, respectively. An arc may also be mimicked by a number of beams at intervals along the arc. A sub-arc is a portion of the arc. It is possible to have continuous sub-arcs, and to stop between sub-arcs.

Monitor Unit (MU) is a measure of the number of particles delivered from the machine. The segment MU is the MU that is delivered in one segment, that is, between two control points. According to established terminology, two consecutive control points define one segment.

The method according to the invention allows for the creation of a treatment plan with a high dose region that conforms closely to the target, while sparing the OARs. The treatment plan for passive ion arc therapy will in most cases also be more robust than active ion arc therapy with respect to organ motion because it enables instantaneous delivery of a flat fluence.

If the range modulating device or the aperture element is allowed to vary, the plan will include different modulations of the beam during the delivery of the arc. Varying the settings of the range modulating device will cause a modulation in depth, whereas varying the aperture means will cause a lateral modulation of the beam. The invention enables the utilization of the degrees of freedom available in ion-based arc therapy.

If the SOBP is allowed to vary, it can be controlled always to provide a flat SOBP, possibly with the range and width changing during the delivery of the arc. Alternatively, the SOBP can be allowed to vary more freely, without or with a relaxed flatness requirement, which means it can be given any suitable shape. The range, width, and shape of the SOBP can be optimized to be constant over the arc, or changing during the delivery of the arc. In contrast to traditional passive ion therapy plans, the SOBP does not have to be flat, which means it can be given any suitable shape.

The method may involve forward planning to generate the plan. Alternatively, the method involves optimization of the plan. In that case, the optimization uses an optimization problem set up to allow variation in settings of at least one of the range modulating device, the aperture element and the segment MU during the delivery of the arc.

In a preferred embodiment, the optimization problem is set up to optimize the arc for at least a first and a second control point, each control point corresponding to a relative angle between the ion beam and the patient, and an isocenter, and to return a plan where the settings for the range modulating device, the MU and/or the aperture element are different for the first and second control point, respectively. It is possible to use more than one control point for the same beam angle and isocenter to provide a more flexible control of the radiation provided to the patient. For increased plan quality, the optimization may involve multi-criteria optimization and/or robust optimization.

Depending on the delivery system, the passive devices may include a range compensator. In that case, the optimization may be set up to allow variation in settings of the range compensator.

The invention also relates to a computer program product, which, when run in a computer will cause the computer to perform the planning method according to the above, to generate a radiotherapy treatment plan for ion-based treatment. The computer program product is preferably stored in a storage means, such as a non-transitory storage means.

The invention also relates to a computer system for performing dose calculations for radiotherapy, the system comprising processing means, said computer system having a program memory having stored therein a computer program product according to the above in such a way that the computer program product, when executed, will control the processing means to perform the dose planning.

The invention also relates to computer program product for controlling the delivery of an ion-based radiotherapy treatment plan by a delivery system, wherein passive devices are used to shape the beam, said passive devices including a range modulating device and an aperture element. The computer program product comprises computer readable code means, preferably stored in a non-transitory storage means, which, when run in a computer, will cause the computer to control the radiotherapy delivery system to deliver an ion beam to a patient, said code means being arranged to cause variation in the settings of at least one of the range modulating device, the aperture element and the MU during the delivery of the beam and to control the movement of the patient and/or the beam in such a way as to create an arc that is continuous or includes at least one continuous sub-arc.

If the radiotherapy delivery system is arranged to provide the beam from a rotatable radiation source, the code means is preferably arranged to cause the computer to control movement of the radiation source relative to the patient.

In one embodiment, the radiation source is fixed, and the patient is placed on a patient support structure that is moveable relative to the beam and the code means is arranged to cause the computer to control movement of the patient support structure relative to the beam. The movement may include relative rotation, translation, or both, between the patient and the gantry.

The code means is preferably arranged to control the at least one passive device to vary the beam characteristics between different control points corresponding to points on the patient.

The invention also relates to radiotherapy delivery system for delivering a passive ion treatment plan wherein an ion beam is delivered to a patient in an arc which is a continuous arc or includes at least one continuous sub-arc, the system comprising a means for providing a fixed beam, a range modulating device for creating a spread out Bragg peak, SOBP, and an aperture element for shaping the beam laterally, the system further comprising a processor and a program memory comprising a computer program product for controlling delivery as described above, arranged to be run in the processor for controlling the delivery of the beam.

The radiotherapy delivery system preferably further comprises a patient support structure arranged to hold the patient and move the patient relative to the fixed beam in such a way that the fixed beam will form an arc, preferably a continuous arc, over at least a part of the patient's body. The patient support structure may be arranged to rotate or tilt the patient so that the fixed beam will enter the patient from different angles and/or move the patient laterally so that the fixed beam will hit the patient at different points along a line.

The arc is achieved by moving the beam and patient relative to each other. This may be achieved by moving only the gantry, only the patient, or both. If only the patient is moved, a more cost-efficient approach for arc therapy is enabled, including a fixed beam line, a passive scattering approach, and a rotating support structure, such as a platform or a chair. An arc can also be achieved by lateral movement of the patient, the gantry, or both. Providing a support structure arranged to move the patient is presently more cost-efficient than providing a moving gantry that is suitable for arc therapy and enables shorter delivery times than what is possible with rotating gantries presently available.

Instead of being placed relative to the beam source, as is common in the art, the range compensator could alternatively be attached to the chair or patient. In the case where the patient is moved relative to the beam, the range compensator could be arranged to rotate with the patient. For a gantry treatment, the range compensator could be similarly attached to the treatment couch or the patient and thus be fixed while the gantry moves. For both a rotating patient and a rotating gantry, this setup allows for different range compensator shapes from different beam angles. The range compensator may be optimized together with any additional parameter that is allowed to vary, and could be differently shaped for different parts of the arc. Such a range compensator could suitably be produced by means of 3D printing.

The method can be combined with any suitable method of robust optimization. It may also be combined with multi-criteria optimization.

BRIEF DESCRIPTION OF THE DRAWINGS

The invention will be described in more detail in the following, by way of example and with reference to the appended drawings, in which.

DETAILED DESCRIPTION

Figure 1:
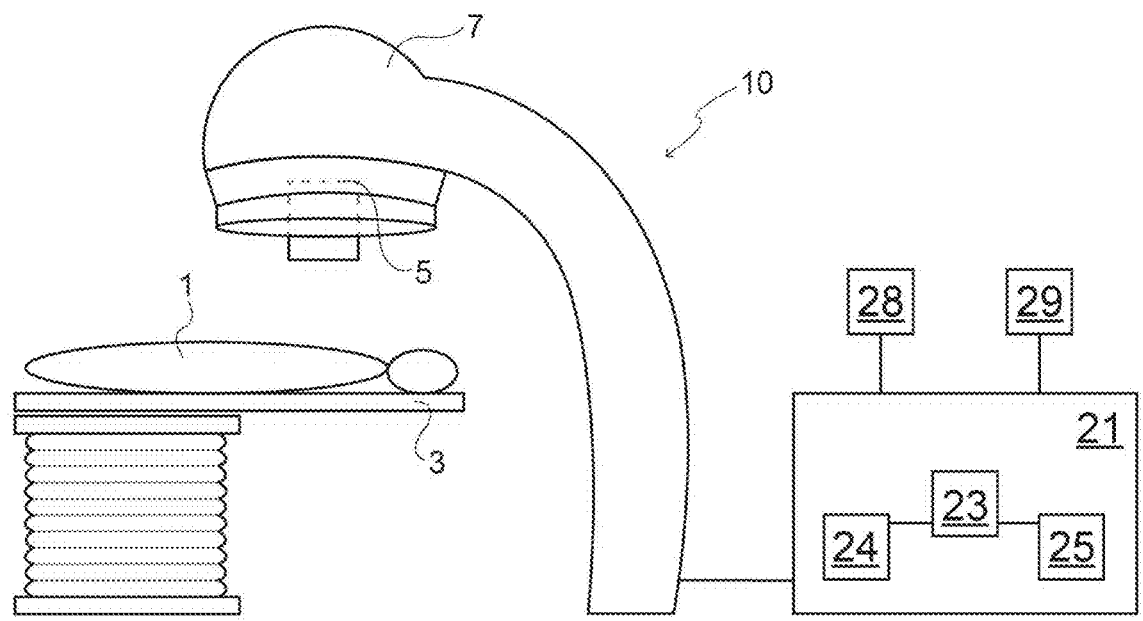
FIG. 1 shows an example of a general dose delivery system

FIG. 1 is an overview of a system 10 for radiotherapy treatment and/or treatment planning. As will be understood, such systems may be designed in any suitable way and the design shown in FIG. 1 is only an example. A patient 1 is positioned on a treatment couch 3. The system comprises a treatment unit having a radiation source 5 mounted in a gantry 7 for emitting radiation towards the patient positioned on the couch 3. Typically, the couch 3 and the gantry 7 are movable in several dimensions relative to each other, to provide radiation to the patient as flexibly and correctly as possible. These parts and their functions are well known to the skilled person. A number of passive devices provided to shape the beam laterally and in depth will be discussed in connection with FIG. 2. The system also comprises a computer 21 which may be used for radiotherapy treatment planning and/or for controlling radiotherapy treatment. As will be understood, the computer 21 may be a separate unit not connected to the imaging unit.

The computer 21 comprises a processor 23, a data memory 24, and a program memory 25. Preferably, one or more user input means 28, 29 are also present, in the form of a keyboard, a mouse, a joystick, voice recognition means or any other available user input means. The user input means may also be arranged to receive data from an external memory unit.

The data memory 24 comprises clinical data and/or other information used to obtain a treatment plan, including a set of clinical goals to be used for planning. The data memory 24 also comprises one or more dose maps for one or more patients to be used in treatment planning according to embodiments of the invention. The program memory 25 holds a computer program, known per se, arranged for treatment plan optimization. The program memory 25 also holds a computer program arranged to make the computer perform the method steps discussed in connection with FIG. 4 or 5 and/or a computer program arranged to make the computer control the radiotherapy treatment of a patient.

As will be understood, the data memory 24 and the program memory 25 are shown and discussed only schematically. There may be several data memory units, each holding one or more different types of data, or one data memory holding all data in a suitably structured way, and the same holds for the program memories. One or more memories may also be stored on other computers. For example, the computer may only be arranged to perform one of the methods, there being another computer for performing the optimization.

Figure 2:
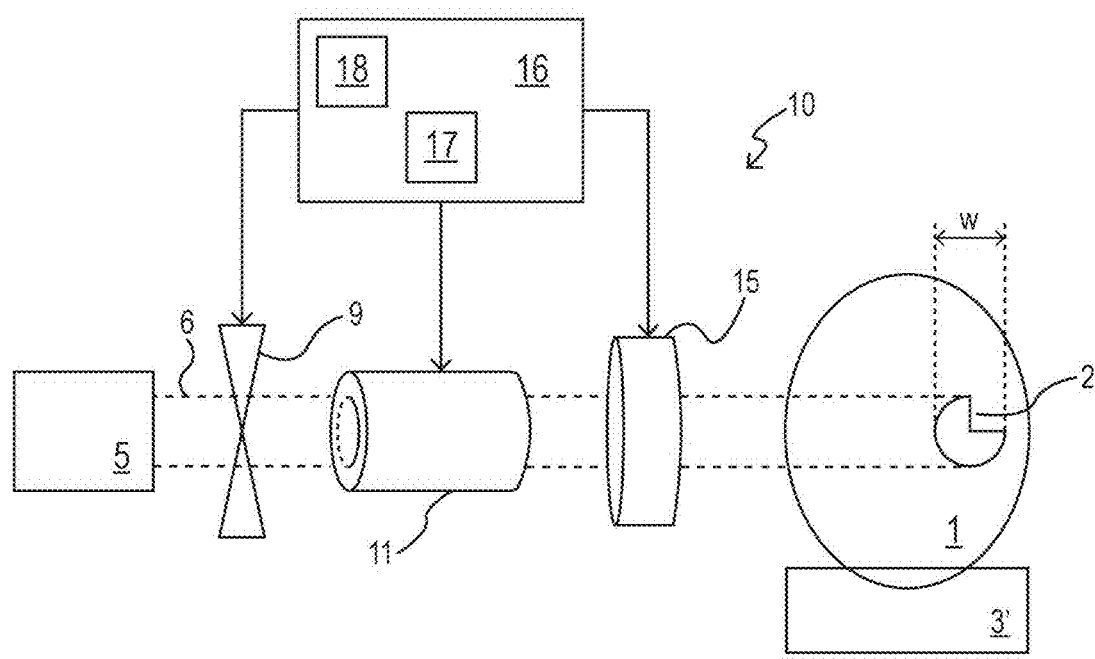
FIG. 2 shows an example of a system for passive ion therapy.

FIG. 2 shows in more detail an example of a delivery system 10 for passive ion therapy in which the invention may be implemented. A patient 1 that is to be subjected to ion therapy is shown schematically to the right in FIG. 2. The patient is placed on a support structure 3', which may be a chair, a couch, a platform or any other suitable support structure. A region of interest ROI, or target 2, within the patient 1 represents the organ or other tissue that is to receive the radiotherapy. The maximum width of the target 2 is marked as w. As is common in the art, there may also be defined critical areas within the patient, which are areas in which it is particularly important to avoid radiation, although this is not shown in FIG. 2.

A radiation source 5 in the form of a gantry provides an ion beam 6 having sufficient energy to achieve the desired maximum range, typically reaching to the distal target 2 edge. Typically, one or two scattering devices (not shown) is arranged to create a broad field of radiation. Alternatively, a uniform scanning technique or wobbling may be used to create a broad field. The dose is subsequently shaped to the target, that is, the region of interest, using passive devices. First, in the path of the radiation, a range modulating device 9 is arranged, in order to create the spread out Bragg peak (SOBP) as will be discussed in more detail in connection with FIG. 3. The range modulating device 9 could be a range modulator, ripple filter or other suitable device. In short, the range modulating device 9 determines the width w' (along the beam direction) of the SOBP, which should be wide enough to cover the area of the target 2. After the range modulating device 9 a beam shaping device 11, shown in FIG. 2 as a block 11, is arranged to shape the beam laterally. The block 11, typically made from brass or some other material that will not be penetrated by the ions, has an aperture 13 for letting the beam through. Instead of the block, another type of device suitable for laterally shaping the beam may be used. Suitable devices include multi-leaf collimators (MLC), jaws, and iris diaphragms.

The beam energy is chosen so that the maximum ion beam range agrees with the most distal point on the target. Of course, more complex patient geometries and target shapes often occur, and the range will be too large for at least some of the target. To compensate for the variation in water equivalent distance to the distal end of the tumour, a range compensator 15 may be introduced to control the local range over the cross-section of the ion beam. Although this is not shown in FIG. 2, the thickness of the range compensator varies across the beam trajectory to adapt the beam energy to the distal end of the target in each point. The range modulating device 9 is arranged to control the depth and to form a spread-out Bragg peak (SOBP).

According to the invention, the radiation is provided as an arc, that is, the beam moves across, or around, the patient. This may be achieved by moving the radiation source relative to the patient or by moving the patient. The arc may extend all the way around the patient, or just a part of the circumference, or along any line along and/or across the patient's body. The arc may be divided into sub-arcs. At least one sub-arc, but preferably the whole arc, is continuous. Typically, one or more control points are defined for the arc, corresponding to different positions on the patient, and defining a set of settings for the beam, including one or more of the passive devices and/or the MU. The control points may be located at predetermined angles or defined in any other suitable way.

The change of the settings of the MU or the passive devices may be controlled in different ways. For arc treatments, the beam is typically on between consecutive control points, and the settings, such as cumulative MU, gantry angle and position, MLC leaf positions, range modulator settings etc, are gradually changed from the current control point settings to the next control point settings. It is also possible, although less efficient, to change the settings while stopping the beam at each gantry angle or position. Of course, it is possible to change only a subset of the settings between control points, the subset comprising one or more of the available settings, or even being empty. For example, the MLC leaf positions may be changed between two control points with identical cumulative MU. This means that the beam will be turned off between the control points. If the control points also have identical beam angles and positions, the beam is stopped at the angle and position. As another example, the cumulative MU may be changed between two control points with identical MLC leaf positions and gantry angles and positions. This means that a static segment will be delivered from the specified gantry angle and position. Although this discussion is focused on an MLC, other beam-shaping devices may be handled in the same way, as a person skilled in the art will realize and be able to implement.

Hence, more than one control point may also be defined for the same position on the patient. In this case, the beam will stop at this position while the other settings are changed to match the control points consecutively. This may be done during radiation, or radiation may be turned on each time new settings have been applied, for the required amount of time.

The delivery system further comprises control means 16 comprising a processor 17 and a program memory 18 comprising a computer program product arranged to control at least one of the range modulating device 9, the lateral beam shaping device 11 and the MU. The control involves changing the settings of at least one of these during the delivery of the arc. The settings of one, any two of them, or all three may be varied to apply at least two different lateral modulations and/or two different modulations in depth and/or two different MU settings as discussed above.

In some embodiments, the range compensator 15 is also arranged to be changed between segments or control points.

The arc may be achieved through movement of the gantry, for example, rotation of the gantry around the patient, or by moving the patient. In the latter case, the patient is placed in a support structure in the form of a chair or a couch or similar, which is arranged to move according to a desired pattern. The support structure may also be a rotating disk on which the patient may stand or be positioned in another suitable way. Additional degrees of freedom can be obtained through translation, pitch, roll, and yaw of the support structure. The chair could rotate continuously or stop at discrete angles and allow the delivery of a few step and shoot segments, or of a DMLC beam from the fixed angle.

The range compensator 15 shown in FIG. 1 could be placed around the patient, or across the area of the patient that will be affected by the beam. If the arc is achieved by movement of the patient, the compensator moves with the patient to expose different shapes for different beam angles. For a rotating gantry, the compensator will be stationary, still exposing different shapes for different beam angles. The compensator could be applied directly on the patient surface as a traditional bolus or mounted on a support structure which is stationary with respect to the patient, i.e. for a rotating patient the support structure and the mounted compensator rotates with the patient. Its thickness could vary in a way that would enable it to function as both a range shifter and a range compensator. It could be calculated by forward planning, always to conform the distal edge of the dose of each arc segment dose to the distal edge of the target, or by optimization, where the dose of each arc segment is allowed to vary more freely to obtain the most beneficial dose distribution with respect to the used optimization functions. The compensator could be produced by 3D printing, or through a more traditional way through milling or drilling.

The plan could be set up either by forward planning for each control point, or preferably through optimization for all control points. According to embodiments of the invention, the SOBP, MU and/or the aperture may be allowed to vary between segments or control points. The shape of the SOBP could be flat or have any other suitable shape to achieve better LET distribution.

If the plan is achieved through optimization, the optimization problem should be defined with respect to aperture, SOBP and MU. The optimization problem may be designed to return a plan using a fixed aperture, that is, the same aperture should be used for all control points. Alternatively, the aperture may be allowed to vary. In this case the same aperture may be optimized for a subset of control points, that is, a sub-arc. Yet another possibility is to optimize different apertures for each control point. This could result in highly modulated plans, such as VMAT for photons, and could enable treatments that conform more closely to the target and spare the organs at risk to a higher degree than less modulated treatments. One disadvantage of such highly modulated plans is that they are more sensitive to delivery during organ motion.

As is known in the art, optimization involves solving an optimization problem, which has the general format shown in Eq. (1).

$$\text{minimize } f(x) \tag{1}$$
$$\text{subject to } x \in X$$

where f(x) is a quality measure of the variables x, and X is the set of allowed variable values.

The skilled person is aware of a number of ways of measuring the quality, for example based on the physical dose or on biological models. As one example, the f(x) can be $$f(x)=g(d(x)) \tag{2}$$

where d(x) is the dose as a function of the variables x and g measures the quality of the dose, for example as $$g(d)=\Sigma_i w_i (d_i - d_i^{ref})^2, \tag{3}$$

where $d_i^{ref}$ is a desired dose level for voxel i and $w_i$ is the importance weight of voxel i. Alternatively, d(x) could be the LET-weighted dose or the RBE-dose, or any other suitable dose-like quantity.

As the skilled person is aware, it would also be possible to consider functions that are dependent on x but not the dose, or that are dependent on both x and the dose, for example as $$f(x)=g(d(x))+h(x) \tag{4}$$

where h is a different quality measure for x, for example, the smoothness of the shape of the MLC or the time required for changing the range and width of the SOBP between neighboring control points.

An example for the set X, given that x=(r, w) are the range and width for the SOBP $$X=\{(r,w): r_{min} \le r \le r_{max}, w_{min} \le w \le w_{max}\} \tag{5}$$

Alternatively, if x=(l, r) are the positions of the left and right leaves, respectively, of an MLC, X could be:

$$X=\{(l,r): l_{min} \le l \le l_{max}, r_{min} \le r \le r_{max}, l+m \le r\} \tag{6}$$

where m is the minimum gap between the left and right leaves.

As the skilled person is aware, there are a number of possible limitations and the ones mentioned above serve only as examples. Other possible limitations include interdigitation and max tip difference for the MLC, as well as limitations to ensure that the leaves do not move faster than the machine allows between consecutive control points, and limitations that the SOBP does not change faster than the machine allows. Typically, x will comprise more variables than r, w or l, r, including such variables as segment weights, control point MU, total arc MU or arc delivery time.

When the optimization problem has been set up, it can be solved in different ways, which are known in the art. Such methods include gradient based methods, using information about the gradient of f with respect to x to determine how x should change, and stochastic method such as simulated annealing or genetic algorithms.

The optimization problem may also be defined to optimize SOBP width and shape to change continuously between control points. In this case, the shape and width can be used to modulate the beam in depth. Alternatively, the SOBP may be optimized to be optimal for all control points or for a subset of control points, that is, a sub-arc.

The shape of the compensator could be optimized with a view to maintaining a suitable range and conformance to distal edge of the target. Alternatively, it could be allowed to vary freely within the limitations of the delivery system to obtain an optimal dose distribution. As mentioned above, the compensator could be placed close to the patient 1 and be adapted to the shape of the target and its distal edge as seen from each point of the compensator.

The optimization problem could include optimization functions based on dose but could alternatively or additionally include other optimization functions based on, for example, LET-related quantities, such as LET or dose-averaged LET, RBE-weighted dose and/or optimization functions aimed at reducing the delivery time.

The method according to the invention may be combined with other known methods of improving dose planning. In particular, special care should be taken to create robust plans. This could be achieved through (a) robust optimization or (b) by creating SFUD (single-field uniform dose) proton arcs, by trying to achieve uniform dose between control points or at discrete angles, or even for a subset of adjacent control points (sub-arc).

Figure 3:
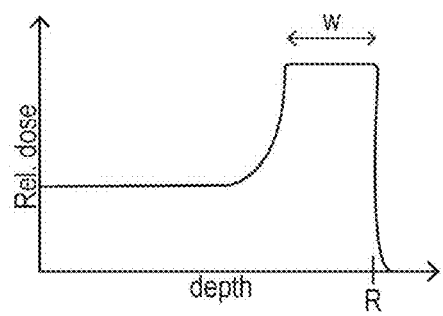
FIG. 3 illustrates an SOBP.

FIG. 3 illustrates schematically the spread-out Bragg peak SOBP of a proton beam within a patient in terms of the relative dose as a function of depth. As can be seen, the dose increases from a plateau region to a maximum, which is constant over a distance w. After the spread out Bragg peak the dose will fall to zero within a short distance. The maximum range of the beam is denoted as R. In one embodiment the maximum dose is arranged to coincide with the target width as shown in FIG. 1, that is, the maximum emitted energy should occur when the proton beam travels through the target, after which the emitted energy should fall to zero as soon as possible. The depth dose shape for other ions is similar to the proton case, except that there will be a low dose tail after the SOBP resulting from nuclear fragments. According to the invention, the shape of the SOBP could be the same for all control points (angles) or change between control points. In contrast to traditional passive ion treatments, where the SOBP is aimed to be flat over the high-dose region, the SOBP could be flat or any other shape to achieve for example better LET distributions.

Figure 4:
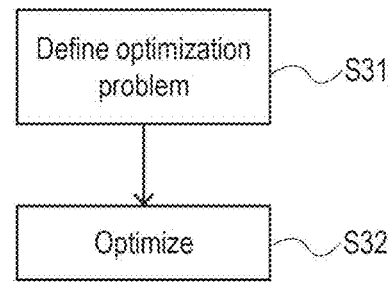
FIG. 4 is an overall flow chart of the method according to a first embodiment of the invention involving optimization.

FIG. 4 is a flow chart defining the steps of an embodiment of the inventive method involving optimization. In step S31, an optimization problem is defined, in the manner described above. The optimization problem is set up to allow variation in settings of the range modulating device, and/or settings of the aperture element during the delivery of the first beam, so that said plan will include modulation of the fluence of the beam during the delivery of the beam. In step S32, the optimization problem is used to optimize a treatment plan.

Figure 5:
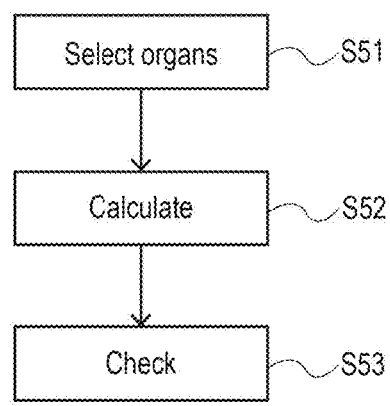
FIG. 5 is an overall flow chart of the method according to a second embodiment of the inventing involving forward planning.

FIG. 5 is a flow chart defining the steps of an embodiment of the inventive method involving forward planning. In step S51, the target and, typically, risk organs are selected. In step S52, for each control point, settings that will result in radiation to the target and not to the risk organs are calculated. The settings, as discussed above, typically include MLC positions, SOBP settings and/or compensator thickness. In step S53, preferably a check is performed to verify that the plan is deliverable, considering the limitations of the delivery system, including such parameters as the speed of the gantry movement and/or the MLC leaves.

Figure 6:
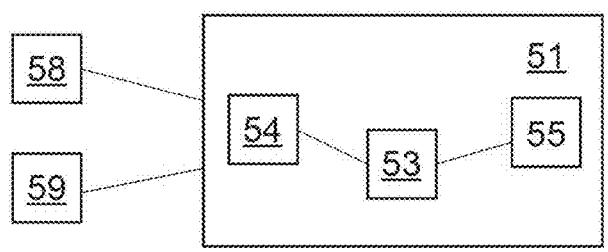
FIG. 6 illustrates a computer system.

FIG. 6 is a schematic representation of a computer system in which the inventive planning method may be performed. A computer 51 comprises a processor 53, a data memory 54 and a program memory 55. Preferably, a user input means 58 is also present, in the form of a keyboard, a mouse, a joystick, voice recognition means or any other available user input means.

The data memory 54 comprises data needed for treatment planning, and typically one or more objective functions. The data in the data memory may be generated in the computer 51, entered by means of the user input means or received from another storage means, in any way known in the art.

As will be understood, the data memory 54 is only shown schematically. There may be several data memory units, each holding one or more different types of data, for example, one data memory for the value set, one for the objective function, etc.

The program memory 55 holds a computer program arranged to control the processor to perform the planning, for example, as defined in FIG. 4 or FIG. 5 or by any other suitable method. It will be understood that not all of the steps of the method of FIG. 5 are necessarily performed in the computer 51.

The invention claimed is:

1. A method of generating a radiotherapy plan for ion therapy designed to expose a patient to ion radiation delivered as a beam, wherein the beam is delivered as an arc, which is a continuous arc or includes at least one continuous sub-arc, and wherein the beam is shaped by means of passive devices including: a range modulating device for creating a spread out Bragg peak, SOBP, and an aperture element for shaping the beam laterally, said method being arranged to allow variation in settings of at least one of the range modulating device, the aperture element and a segment MU during the delivery of the beam, wherein the passive devices include a range compensator which is placed around the patient or across the area of the patient that will be affected by the beam, the method involving optimization, wherein the optimization uses an optimization problem set up to allow variation in settings of the range compensator.

2. The method according to claim 1, involving forward planning.

3. The method according to claim 1, wherein the optimization problem is set up to allow variation in settings of at least one of the range modulating device, the aperture element and the segment MU during the delivery of the arc.

4. The method according to claim 3, wherein the optimization problem is set up to optimize the arc for at least a first and a second control point, each control point corresponding to a relative angle between the beam and the patient, and an isocenter, and to return a plan where the settings for the range modulating device, the MU and/or the aperture element are different for the first and second control point.

5. The method according to claim 4, wherein more than one control point is used for the same gantry angle and isocenter.

6. The method according to claim 3, involving multi-criteria optimization and/or robust optimization.

7. A computer program product, stored in a non-transitory storage means which, when run in a computer will cause the computer to perform the method of claim 1.

8. A computer system for performing dose calculations for radiotherapy, the system comprising processing means, said computer system having a program memory having stored therein a computer program product according to claim 7 in such a way that the computer program product, when executed, will control the processing means to perform the dose planning.

9. A computer program product comprising computer readable code means, stored in a non-transitory storage means, which, when run in a computer, will cause the computer to control a radiotherapy delivery system to deliver an ion beam to a patient, wherein passive devices are used to shape the beam, said passive devices including a range modulating device and an aperture element said code means being arranged to cause variation in the settings of at least one of the range modulating device, the aperture element and the MU during the delivery of the beam and to control the movement of the patient and/or the beam in such a way as to create an arc, wherein the arc is a continuous arc or includes at last one continuous sub-arc, the passive devices further including a range compensator which is placed around the patient or across the area of the patient that will be affected by the beam, and the optimization being set up to allow variation in settings of the range compensator.

10. The computer program product according to claim 9, wherein the radiotherapy delivery system is arranged to provide the beam from a rotatable radiation source and the code means is arranged to cause the computer to control movement of the radiation source relative to the patient.

11. The computer program product according to claim 9, wherein the radiation source is fixed and the patient is placed on a patient support structure that is moveable relative to the beam and the code means is arranged to cause the computer to control movement of the patient support structure relative to the beam.

12. The computer program product according to claim 9, wherein the code means is arranged to control the at least one passive device to vary the beam characteristics between different control points corresponding to points on the patient.

13. A radiotherapy delivery system for delivering a passive ion treatment plan wherein an ion beam is delivered to a patient in an arc, wherein the arc is a continuous arc or includes at last one continuous sub-arc, the system comprising a means for providing a fixed beam, a range modulating device for creating a spread out Bragg peak, SOBP, and an aperture element for shaping the beam laterally, the system further comprising a processor and a program memory comprising a computer program product according to claim 10 arranged to be run in the processor for controlling the delivery of the beam.

14. The radiotherapy delivery system according to claim 13, further comprising a patient support structure arranged to hold the patient and move the patient relative to the fixed beam in such a way that the fixed beam will form an arc over at least a part of the patient's body.

* * * * *